United States Patent [19]

Rooks, II

[11] 3,947,479

[45] Mar. 30, 1976

[54] REDUCTION OF SERUM LIPID LEVELS, AND AGENTS AND COMPOSITIONS USEFUL THEREFOR

[75] Inventor: Wendell H. Rooks, II, Los Altos, Calif.

[73] Assignee: Syntex (U.S.A.) Inc., Palo Alto, Calif.

[22] Filed: Nov. 21, 1973

[21] Appl. No.: 417,972

Related U.S. Application Data

[63] Continuation-in-part of Ser. No. 315,997, Dec. 18, 1972, abandoned.

[52] U.S. Cl....... 260/397.4; 424/238; 260/239.55 R
[51] Int. Cl.².......................................... C07J 3/00
[58] Field of Search................................ 260/397.4

[56] References Cited
OTHER PUBLICATIONS
Cross et al., "JACS," Vol. 86 (1964) p. 1221.

*Primary Examiner*—Elbert L. Roberts
*Attorney, Agent, or Firm*—Joseph I. Hirsch; William B. Walker

[57] ABSTRACT

A method for lowering elevated serum lipid concentrations comprising administering a composition containing, as the active ingredient, a 3$\beta$-substituted-16$\alpha$-cyanopreg-5-en-20-one wherein the substituent at the 3$\beta$-position is selected from the group consisting of hydroxy, alkoxy having 1 to 6 carbon atoms, cycloalkoxy having 3 to 6 carbon atoms, acyloxy wherein the acyl moiety has 2 to 7 carbon atoms, tetrahydrofuran-2'-yloxy, tetrahydropyran-2'-yloxy, and 4'-alkoxytetrahydropyran-4'-yloxy where the alkoxy moiety has 1 to 6 carbon atoms. Representative active ingredients are 3$\beta$-acetoxy-16$\alpha$-cyanopreg-5-en-20-one and 3$\beta$-cyclopentyloxy-16$\alpha$-cyanopregn-5-en-20-one. These representative agents are also useful in the therapeutic method of protecting and regenerating damaged hepatic tissue.

2 Claims, No Drawings

REDUCTION OF SERUM LIPID LEVELS, AND AGENTS AND COMPOSITIONS USEFUL THEREFOR

REFERENCE TO PARENT APPLICATION

This application is a continuation-in-part application of application Ser. No. 315,997, filed Dec. 18, 1972, and now abandoned.

FIELD OF THE INVENTION

This invention relates to a method for lowering elevated serum lipid concentrations, and to agents and compositions useful therefor. IN addition, this invention relates to a method of protecting and regenerating damaged hepatic tissue.

SUMMARY OF THE INVENTION

This invention relates to compounds represented by the formula:

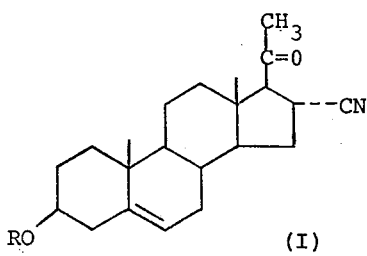

where R is hydrogen, alkyl having 1 to 6 carbon atoms, cycloalkyl having 3 to 6 carbon atoms, acyl having 2 to 7 carbon atoms, tetrahydropyran-2'-yl, tetrahydrofuran-2'-yl, or 4'-alkoxy-tetrahydropyran-4'-yl where the alkoxy moiety has 1 to 6 carbon atoms, and the use thereof as the active ingredient in a method for lowering elevated serum lipid concentrations. Certain of the above compounds are known compounds which fall into the category of compounds generally known as catatoxic steroids [see Hans Selye, *Rev. Can. Biol.* 29, No. 1, 49 (1970); *Hormones*, 2(3), 129 (1971); *Experientia* 27(12), 1445 (1971)]. However, the remaining compounds, as represented by the following formula, are believed to be novel:

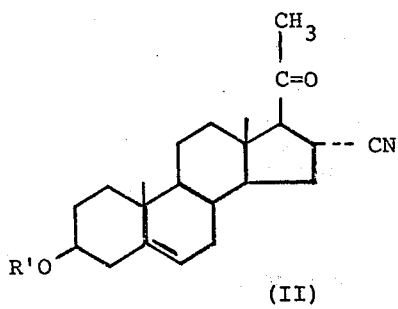

where R' is cycloalkyl, having 3 to 6 carbon atoms.

Compounds falling within the scope of Formulas I and/or II include 3β-acetoxy-16α-cyanopregn-5-en-20-one and 3β-cyclopentyloxy-16α-cyanopregn-5-en-20-one.

Other representative compounds of Formula I include 3β-hydroxy-16α-cyanopregn-5-en-20-one, 3β-methoxy-16α-cyanopregn-5-en-20-one, 3β-tetrahydropyran-2'-yloxy-16α-cyanopregn-5-en-20-one, 3β-tetrahydrofuran-2'-yloxy-16α-cyanopregn-5-en-20-one and 3β-(4'-methoxy-tetrahydropyran-4'-yloxy)-16α-cyanopregn-5-en-20-one.

The present invention is also directed to pharmaceutical compositions comprising a pharmaceutically effective amount of a compound of Formula I or II above in admixture with a pharmaceutically acceptable non-toxic carrier.

An amount of the compound of Formula I or II effective for the reduction of serum lipid levels, in accordance herewith, can vary generally in the range of from 0.01 mg. to about 20 mg. per kg. of host body weight per day, preferably from 0.1 mg. to about 5 mg. The active compound hereof can be administered in any suitable manner, parenteral or oral, and in any form suitable for the administration mode, isotonic solutions, suspensions, tablets, capsules, and the like.

The present invention is suitable for those mammalian hosts, including man and domestically useful animals or pets, suffering from disease states in which high serum lipid levels are manifested, particularly elevated triglycerides, and/or cholesterol levels.

Useful pharmaceutical carriers for the preparation of the compositions hereof, can be solids, liquids or gases. Thus, the compositions can take the form of tablets, pills, capsules, powders, sustained release formulations, solutions, suspensions, elixirs, aerosols and the like. The carriers can be selected from the various oils, including those of petroleum, animal, vegetable or synthetic origin, for example, peanut oil, soybean oil, mineral oil, sesame oil and the like. Water, saline, aqueous dextrose and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glyceryl monostearate, sodium chloride, dried skim milk, glycerol, propylene glycol, water and the like. Suitable pharmaceutical carriers and their formulation are described in "Remington's Pharmaceutical Sciences" by E. W. Martin. Such compositions will, in any event, contain an effective amount of the active compound together with a suitable amount of carrier so as to prepare the proper dosage form for proper administration to the host.

The compounds of Formula I or II above are also useful as agents in the therapeutic recovery or restoration of damaged hepatic tissue.

Hepatic disorders are an ever increasing health problem. Disorders of the liver can be viral in origin, causing hepatitis, or very commonly the result of heavy ingestion of ethyl alcohol which may bring about liver cirrhosis. Each of these conditions is manifested by damaged hepatic tissue which, if left to progress, can seriously impair liver function and lead to ultimate death of the organism. Although the liver itself possesses remarkable healing ability after damage, continual challenge is often inflicted, as, for example, in the case of alcoholism, which results in the degenerative conditions referred to above.

In view of these problems, efforts have been made to aid organisms in recovery or cure of hepatic degenerative conditions. Corticosteroids have been found to be useful in the treatment of liver disease presumably because of their anti-inflammatory activity. Recently Selye has described a group of agents called catatoxic steroids which are not anti-inflammatory but which protect the organism agsinst certain toxins probably by induction of certain specific hepatic enzymes. See Hans Selye, "Defensive Steroids", *Hormones*, 2(3), 129, (1971).

Thus, it has been found that pretreatment of an organism with certain catatoxic steroids, including 16α-cyanopregn-5-en-3β-ol-20-one, protects against subsequent administration of specific toxicants, e.g., indomethacin and digitoxin, the protective effect being manifested relatively rapidly to provide prophylactic activity in the case of acute or slow poisoning. See Hans Selye, "Effect of Catatoxic Steroids Upon Established Morbid Changes", *Experientia*, 27/12, 1445 (1971). Protection is provided by more rapid metabolic destruction of the toxicants. Although many compounds have been tested for such prophylactic protection from toxicants—see Hans Selye, *Rev. Can. Biol.*, 29, No. 1, 49 (1970) —an activity-structure relationship for compound types has not been clearly established. Further, as of the date of this invention, Selye has not taught the protection of the liver as an organ.

Thus, although spironolactone has been found to increase liver weight and mitotic activity in rats —see *Klinische Wochenschrift*, 48(6), 385 (1970)—the tests reported were conducted without toxin challenge and lack a demonstration of effect on damaged hepatic tissue.

It has now been discovered that the compounds of Formula I or II above exhibit activity different in kind and/or degree from that described heretofore, that is, the compounds of Formula I or II afford actual therapeutic recovery or normalization of damaged hepatic tissue, in unexpectedly enhanced degree, when administered in an effective amount to a host, as opposed to the prophylactic activity (in tissues other than the liver) for certain of the catatoxic steroids as taught by Selye, supra. The 3β-acetoxy-16α-cyanopregn-5-en-20-one of Formula I and 3β-cyclopentyloxy-16α-cyanopregn-5-en-3-one of Formula II are particularly useful agents for this utility.

Therapeutic compositions of the type and composition, as set forth above with respect to the compositions for the reduction of serum lipid levels, are also considered to be within the scope of this aspect of the present invention. Administration can also be as set forth above, and is suitable for those mammalian hosts, including man and domestically useful animals or pets, suffering from the hepatically toxic effects of a broad class of aflatoxins and mycotoxins and (living) organisms, e.g., viruses. Of particular importance is the use of the agents of the present invention as a curative of liver damage suffered from the effects of alcoholism especially where the liver can be characterized as a fatty (as opposed to fibrotic) liver.

To the extent that the host, for example an alcoholic, has both liver damage and elevated serum lipid levels, the agents of Formula I or II above can be used to treat both conditions, and, to the extent that the liver has not become fibrotic, effective results can be achieved against both conditions. It is important to note that this protection occurs despite continued intake of alcohol and is not due to more rapid metabolic destruction of the alcohol.

The compounds of Formula II can be prepared by treating 3β-hydroxy-16α-cyanopregn-5-en-3-one in an inert organic solvent, such as benzene, with sodium hydride, followed by addition of a halo derivative of the R' moiety defined above, for example, cyclopentyl bromide in the case of the preparation of 3β-cyclopentyloxy-16α-cyanopregn-5-en-3-one. The desired product is recovered from the reaction mixture and purified, by conventional techniques known to those skilled in this art.

The following examples illustrate the manner by which the present invention can be practiced.

EXAMPLE 1

A solution of one chemical equivalent of 16α-cyanopregn-5-en-3β-ol-20-one in 30 ml. of benzene is heated to reflux and about 2 ml. removed by distillation to eliminate moisture. The mixture is cooled to room temperature and two chemical equivalents of sodium hydride are added, followed by the dropwise addition of two chemical equivalents of cyclopentyl bromide in 10 ml. of benzene over a period of 20 minutes. The mixture is allowed to reflux for 20 hours after which time the precipitate of sodium bromide is removed by filtration and the organic phase dried and evaporated to yield 3β-cyclopentyloxy-16α-cyanopregn-5-en-20-one which is further purified upon recrystallization for pentane.

In similar manner, substituting an appropriate reactant for the cyclopentyl bromide, the other compounds of Formula II above are prepared.

EXAMPLE 2

Female Simonsen albino rats (120 to 140 grams) are used to test for inhibition of carbon tetrachloride ($CCl_4$) induced fatty liver. Beginning on day 1, three dosage groups of seven animals each receive daily subcutaneous injections of $CCl_4$ (0.1 ml./100 g. body weight based on animal weight on day 1) (vehicle: sesame oil 1:1) for seven consecutive days (1 to 7). The test material, 3β-acetoxy-16α-cyanopregn-5-en-20-one, is administered (vehicle: 1.0 ml. CMC/dose) to the three groups orally twice a day on days 8 to 14 (total 7-day dose, 0.05 mg., 0.5 mg. and 5 mg., respectively). Two control groups of seven animals each are used, each not receiving test material, and one group receiving $CCl_4$ and the other not. The control animals are sacrificed on day 8, the test animals on day 15, with hepatectomization. A further control group of seven animals receives $CCl_4$, as above, on days 1–7, and then receives a dose of the CMC vehicle suspension on days 8–14. This group is also sacrificed on day 15, with hepatectomization. A 500 mg. portion of each liver is digested and the lipid content determined using a modification of the procedure of Baruch et al., Proc. Soc. Exptl. Biol. Med., 86, 79 (1954).

On day 8, the lipid residue of the control group receiving $CCl_4$ is significantly higher than that of the negative control group. Significant reduction of $CCl_4$ induced increase in lipid residue is obtained in the groups receiving the test material, when compared with controls. The serum glutamic pyruvic transaminase (SGPT) level of the control group receiving $CCl_4$ is higher than that of the negative control group. The test groups showed a return of the SGPT levels to normal on day 15. The above procedure is repeated using 3β-cyclopentyloxy-16α-cyanopregn-5-en-20-one, with similar results.

EXAMPLE 3

Male Simonsen albino rat (180–200 grams) are used to test for inhibition of ethanol induced elevation of serum and liver triglyceride levels. Beginning on day 1, each of the animals in three dosage groups of six animals each and three dosage groups of seven animals each orally receive an ethanol solution (6 g. of 95% ethanol diluted with distilled water to 28 ml., administered at a dose of 28 ml. per kg. of animal body weight) daily on days 1–21. On day 15, the animals on one group of six are sacrificed with hepatectomization and collection of blood. The test material, 3$\beta$-cyclopentyloxy-16$\alpha$-cyanopregn-5-en-3one, is administered orally (vehicle: 1.0 ml. CMC/dose) to four dosage groups (the first three groups having seven animals each, the fourth group having only 6 animals) twice a day on days 15–21 (total dose 0.02 mg., 0.1 mg., 0.5 mg. and 2.5 mg., respectively). On the morning of day 22, the animals are sacrificed with hepatectomization and collection of blood.

The livers are homogenized and processed according to the method of Butler et al., J. Lipid Research, Vol. 2, 95 (1961). The blood is processed according to the method of Van Handel, Clinical Chemistry, Vol. 7, 249 (1961).

The ethanol as given markedly increased both hepatic and serum triglyceride levels. The test material elicited dose-related inhibition of the elevation of the triglyceride content of both liver and serum, when compared to the ethanol-receiving control groups. When serum ethanol levels were determined shortly after ingestion of alcohol, the differences were found between the control group and the drug-treated group. Therefore, alcohol metabolism was not increased.

EXAMPLE 4

Example 3 is repeated with one group of seven animals receiving a total test material dose of 0.004 mg., a second group of six animals receiving a total test material dose of 0.02 mg., a third group of seven animals receiving a total test material dose of 0.1 mg., and a fourth group of five animals receiving a total test material dose of 0.5 mg. As with the assay described in the preceeding example, the ethanol markedly increased both hepatic and serum triglyceride levels. These levels were substantially normalized by the doses of test material.

EXAMPLE 5

Female Simonsen albino rats (170–190 grams) are used to test for inhibition of lard induced elevation of serum triglyceride levels. Beginning on day 1, 2 dosage groups of 10 animals each are placed on a diet of Purina Laboratory Chow and 2 other dosage groups of 10 animals each are placed on a diet of Simonsen Laboratories special lard diet containing 10% lard. Beginning on day 15, the animals in one dosage group receiving the Purina chow and the animals in one dosage group receiving the Simonsen 10% lard diet are given the test material, 3$\beta$-cyclopentyloxy-16$\alpha$-cyanopregn-5-en-20-one, administered orally (vehicle: 1.0 ml. CMC/dose) twice daily (total dose: 2.5 mg.). On day 22, the animals are sacrificed with hepatectomization and blood collection. Liver and triglyceride processing is according to the methods referred to in Example 3 above.

The test material reduced the elevation of the hepatic triglyceride level caused by the Simonsen 10% lard diet, but the hepatic triglycerides of the animals receiving the test material and the Purina Chow was above the control levels. Serum triglyceride levels in those animals receiving Purina Chow were lowered by the test material, but the test material did not have the same significant effect on those animals receiving the Simonsen lard diet, although the levels were slightly lower than the control levels. The control animals fed the Simonsen lard diet had elevated serum cholesterol levels which were normalized by the test material.

EXAMPLE 6

Twelve male, retired breeder, Sprague-Dawley rats were placed on a normal Purina Rat Chow diet for a three week normalization period. The baseline values of their blood lipids were determined by micro analysis of blood plasma obtained from puncturing the tail vein. Total plasma triglyceride was measured by a micromodification of the method of Eggstein [Klin. Wschr., Vol. 44, 267 (1966)].

After the rats had spent three weeks under normal conditions, they were divided into two groups of six each. The animals of Group I were given a daily oral dose of the CMC suspension vehicle only. The animals of group II were given, for 7 consecutive days, a daily oral dose of 3$\beta$-cyclopentyloxy-16$\alpha$-cyanopregn-5-en-20-one suspended in CMC solution in such an amount that each rat received 1.0 mg. per kg. per day of test material. Blood samples were collected by tail vein puncture on the eighth day. Plasma triglycerides were then determined for each group. Average total plasma triglycerides for the control group were 159 mg. % and for the group II animals were 115 mg. %. This data represents a statistically significant reduction in plasma triglycerides due to use of the test material.

EXAMPLE 7

Tablets suitable for oral daministration and containing 5 to 100 mg. of 3$\beta$-acetoxy-16$\alpha$-cyanopregn-5-en-20-one or 3$\beta$-cyclopentyloxy-16$\alpha$-cyanopregn-5-en-20-one, are prepared as follows:

| Components: | |
|---|---|
| 3$\beta$-acetoxy-or-cyclopentyloxy-16$\alpha$-cyanopregn-5-en-20-one | 5–100 mg. |
| corn starch | 25 mg. |
| povidone | 1–10 mg. |
| methanol | 0.065 ml. |
| magnesium stearate | 0.5 mg. |
| spray dried lactose | q.s. 80–150 mg. |

3$\beta$-Cyclopentyloxy-16$\alpha$-cyanopregn-5-en-20-one (5-100 mg.) is mixed with 25 mg. of corn starch and 80-150 mg. of spray dried lactose. Povidone (1-10 mg.) is dissolved in 0.065 ml. of methanol. The 3$\beta$-cyclopentyloxy-16$\alpha$-cyanopregn-5-en-20-one, corn starch, lactose mixture is granulated with the povidone and methanol solution. The granulation is passed through a No. 12 mesh screen and then dried at 37°–40°C. The dried granulation is then passed through a No. 16 mesh screen. Magnesium stearate (0.5 mg.) is then added and the resultant components are mixed thoroughly. The mixture is processed by a punched tablet machine to produce tablets suitable for oral administration.

The above procedure is repeated using 3$\beta$-acetoxy-16$\alpha$-cyanopregn-5-en-20-one.

Reduction of carbon tetrachloride induced or ethanol induced lipid residue increase, normalization of (SGPT) enzyme levels in rat hepatic tissue and inhibition of the elevation of triglyceride content in serum and hepatic tissue in rats can be regarded as representative of and translatable to the therapeutic restoration of damaged hepatic tissue, particularly ethanol induced fatty liver tissue, in man.

While the present invention has been described with reference to specific embodiments thereof, it should be understood by those skilled in this art that various changes may be made and equivalents may be substituted without departing from the true spirit and scope of the invention. In addition, many modifications may be made to adapt a particular situation, material or composition of matter, process, process step or steps, or then-present objective to the spirit of this invention without departing from its essential teachings.

What is claimed is:

1. A compound selected from the group of compounds represented by the formula:

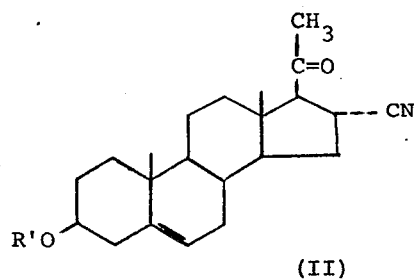

(II)

where R' is cycloalkyl having 3 to 6 carbon atoms.

2. The compound of claim 1 wherein said compound is 3β-cyclopentyloxy-16α-cyanopregn-5-en-20-one.

* * * * *